US006520928B1

(12) United States Patent
Junior

(10) Patent No.: US 6,520,928 B1
(45) Date of Patent: Feb. 18, 2003

(54) MEDICAL LIQUID INJECTION SYSTEM AND METHOD

(76) Inventor: Alceu Meibach Rosa Junior, Rua da Contagem, 206-Saude, São Paulo, SP CEP 04.146-100 (BR)

( * ) Notice: Subject to any disclaimer, the term of this patent is extended or adjusted under 35 U.S.C. 154(b) by 0 days.

(21) Appl. No.: 09/377,470

(22) Filed: Aug. 19, 1999

(51) Int. Cl.[7] ................................................. A61M 1/00
(52) U.S. Cl. ........................................ 604/30; 604/152
(58) Field of Search .................... 604/30, 67, 150–153, 604/131, 140, 181, 182, 245

(56) References Cited

U.S. PATENT DOCUMENTS

| 4,613,328 A | 9/1986 | Boyd |
| 4,747,824 A | 5/1988 | Spinello |
| 4,787,893 A | 11/1988 | Villette |
| 5,176,646 A | 1/1993 | Kuroda |
| 5,180,371 A | 1/1993 | Spinello |
| 5,456,670 A | 10/1995 | Neer et al. |
| 5,647,851 A | 7/1997 | Pokras |
| 5,672,155 A | 9/1997 | Riley et al. |
| 5,690,618 A | 11/1997 | Smith et al. |

FOREIGN PATENT DOCUMENTS

| BR | 7502580-9 | 2/1997 |
| BR | 9505141-4 | 3/1997 |
| ES | 1034904 | 7/1997 |

OTHER PUBLICATIONS

English Translation BR PI 9505141–4.

Primary Examiner—Manuel Mendez
(74) Attorney, Agent, or Firm—Schweitzer Cornman Gross & Bondell LLP

(57) ABSTRACT

A novel device and method for the efficient, regular and highly maneuverability administration of medical liquids, especially anesthetics. The system of the present invention includes a light-weight, hand-held injection device which is connected to an operating pedal and a control unit. The control unit stores a number of preprogrammed injection procedures having specific injection flow rates and volumes, and provides the user with the ability to create and store a plurality of user-defined procedures. The control unit and injector allow precise selection, control and monitoring of the injection flow rate and volume. The operating pedal provides "hands-free" control of the procedures, as well as a means to select various sub-procedures, such as an Aspiration mode, Introduction mode, or Preparation mode, in addition to the Injection mode.

28 Claims, 15 Drawing Sheets

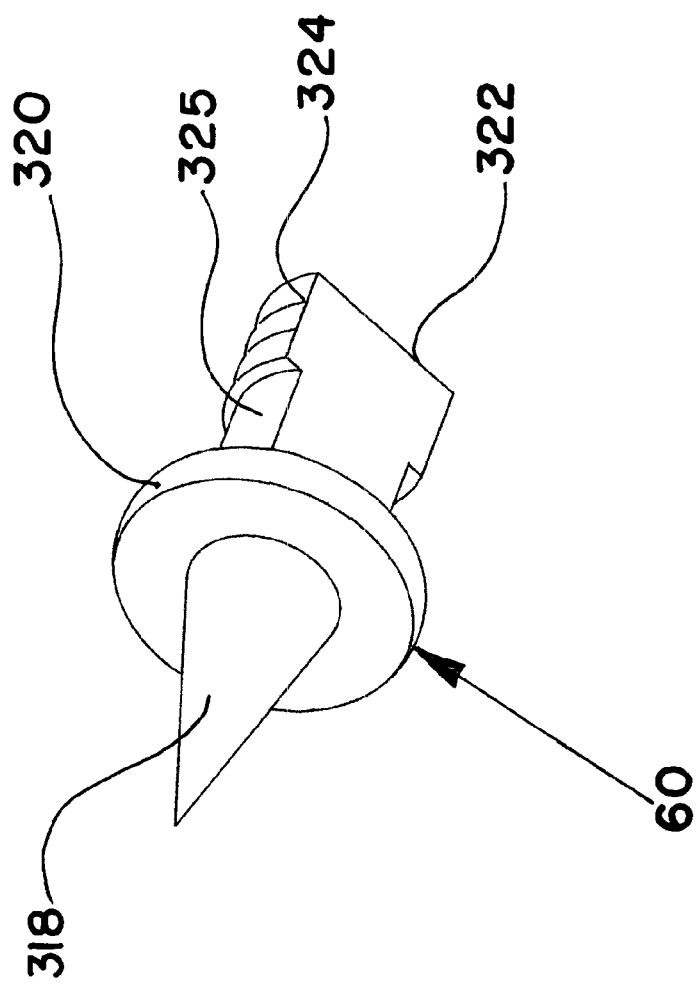

MEDICAL LIQUID INJECTION SYSTEM AND METHOD

FIELD OF THE INVENTION

This invention pertains to the field of medical liquid injection systems and, in particular, to programmable medical liquid injection systems.

BACKGROUND AND SUMMARY OF THE INVENTION

Medical liquid injection devices are currently used to administer medical liquids, such as anesthetics. However, prior medical liquid injection devices lack the desired precision, regularity and maneuverability to be of substantial use to medical practitioners, especially in the field of dentistry.

The present medical liquid injection system provides a novel device and method for the efficient, regular and highly maneuverability administration of medical liquids, especially anesthetics. The system of the present invention includes a lightweight, balanced, hand-held injection device which is connected to an operating pedal and a control unit. The control unit stores a number of preprogrammed injection procedures having specific injection flow rates and volumes, and provides the user with the ability to create and store a plurality of user-defined procedures. The control unit and injector allow precise selection, control, monitoring and adjustment of the injection flow rate and volume. The operating pedal provides "hands-free" control of the procedures, as well as a means to select various sub-procedures, such as an Aspiration mode, Introduction mode, or Preparation mode, in addition to the Injection mode.

BRIEF DESCRIPTION OF THE DRAWINGS

For a complete understanding of the above and other features of the invention, reference shall be made to the following detailed description of the preferred embodiments of the invention and to the accompanying drawings, wherein:

FIG. 8A is an enlarged view of the harpoon;

DETAILED DESCRIPTION OF THE INVENTION

Figure 1:
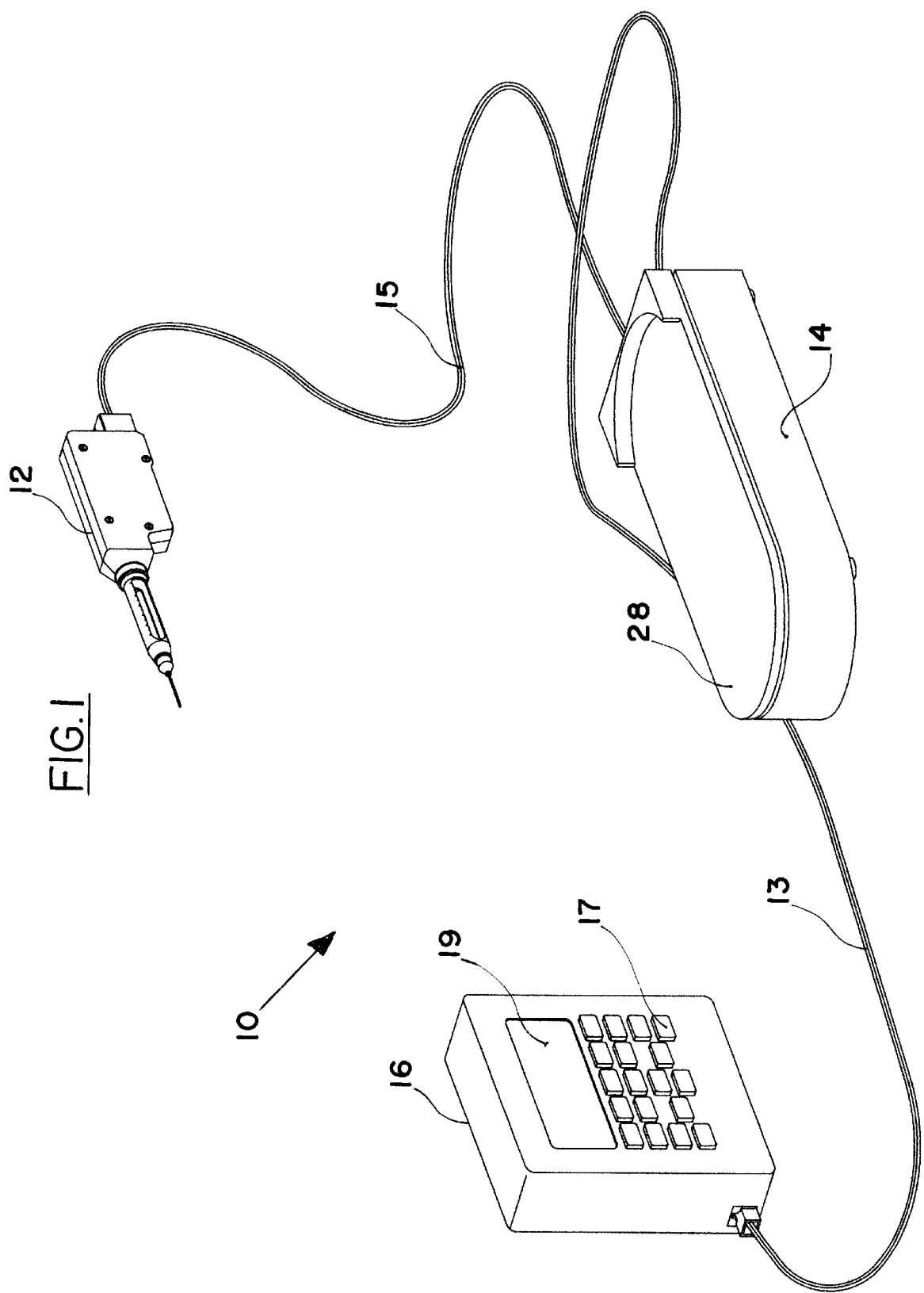
FIG. 1 is a schematic diagram of the medical liquid injection system of the present invention.

Referring to the drawings, and initially to FIG. 1 thereof, the medical liquid injection system 10 of the present invention includes three primary components: The injection device 12, the operating pedal 14 and the control unit 16. The injection device 12 and the control unit 16 are connected to the operating pedal 14 by shielded cables 13, 15, which provide power to the control unit 16 and injection device 12 and transmit information and control signals among the components.

The injection device 12 is of a reduced size, with a pen-like configuration and a reduced, balanced weight. This allows a high degree of maneuverability and accuracy in the use of the injection device 12, especially during extended or successive procedures. The operating pedal 14 contains four switches which are operated by pressing on the toe or heel, or either side of the foot pad 28. Thus, the foot pad 28 provides four separate controls which are conveniently accessible. The control unit 16 includes a keyboard 17 for entering data and selecting procedures, a display readout 19, and a sound producing device (not shown), such as a speaker.

Figure 2:
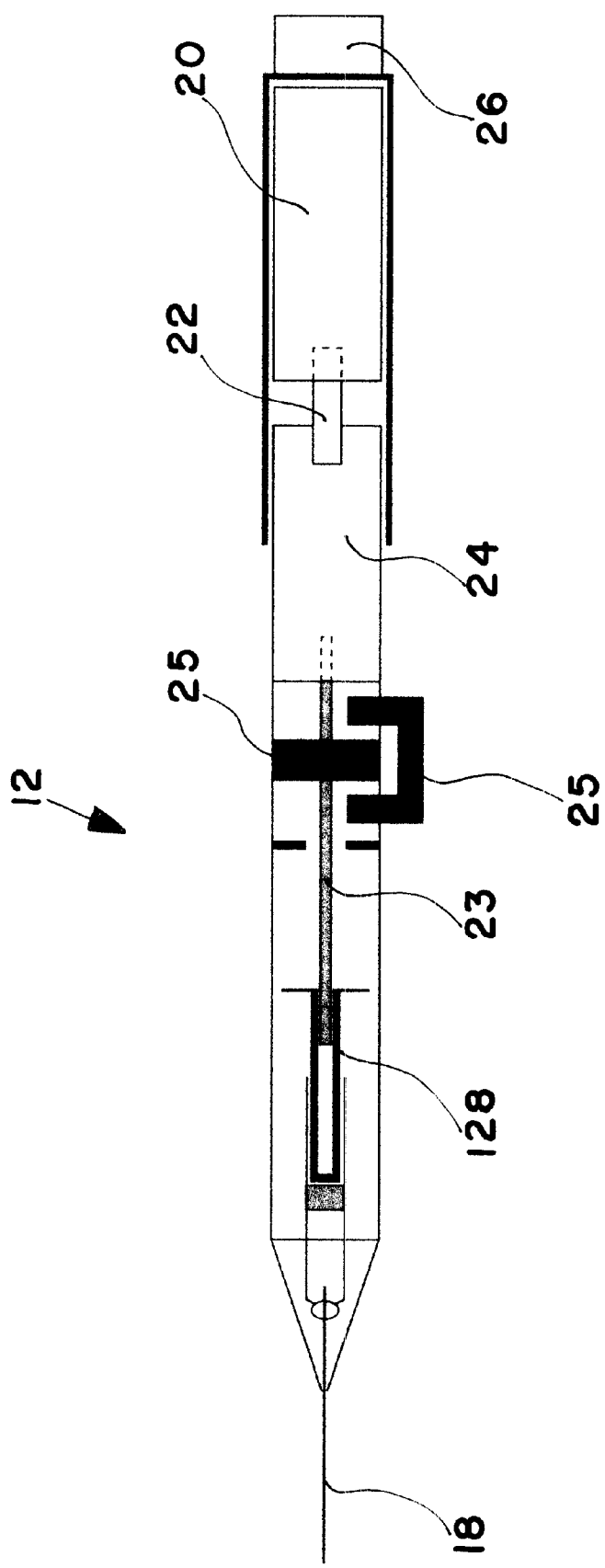
FIG. 2 is a schematic diagram of the injection device of FIG. 1.
Figure 3:
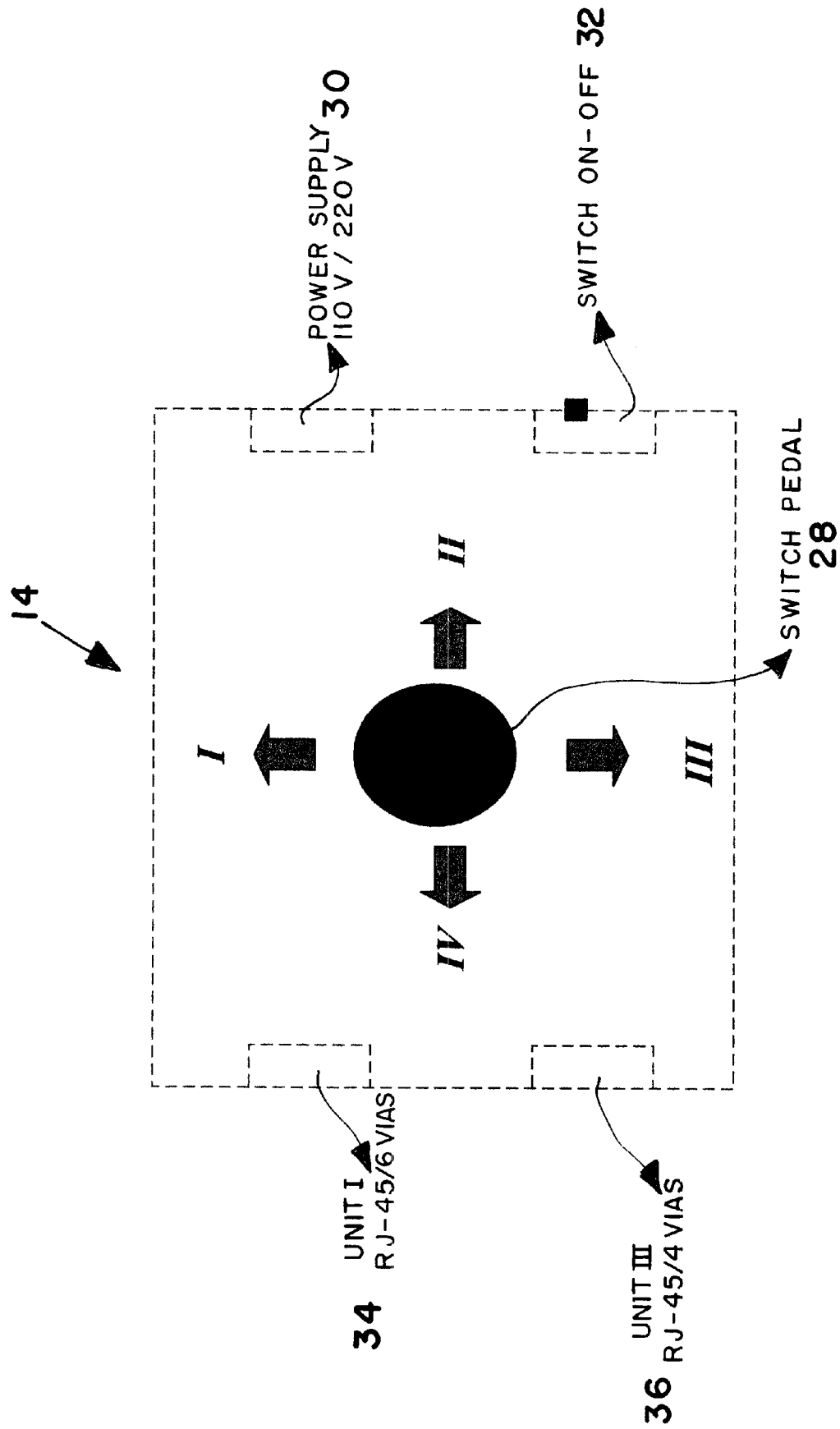
FIG. 3 is a schematic diagram of the operating pedal of the injection device of FIG. 1.

Referring to FIG. 2, the injection device 12 includes a needle 18, a motor 20 having a drive shaft 22, a reducer 24 connected to the drive shaft 22, a threaded shaft 23 connected to the reducer 24, and a motion sensor 25 which senses the motion of the threaded shaft 23 induced by the motor 20 and reducer 24. The threaded shaft 23 imparts forward and backward movement to a hollow piston 128 which is threaded internally. The injection device 12 also includes an connection port 26 for receiving electrical power and motor control signals from the operating pedal 14, and for transmitting the signal generated by the motion sensor 25 to the operating pedal 14. Through the motion sensor 25, the injection system 10 precisely monitors and adjusts, if necessary, the flow rate and volume of liquid expelled from the needle 18.

Referring to FIGS. 3–4 and 10–13, the operating pedal 14 includes a foot pad 28, which is pivotal in two substantially orthogonal axes generally toward the four primary points of a compass, that is up, down, right and left. The operating pedal 14 also includes a power supply port 30, an on/off switch 32, and two connection ports 34, 36 for transmitting power and control signals to and from the injection device 12 and control unit 16. The operating pedal 14 also includes a dual transformer for supplying reduced voltages to the injection device 12 and control unit 16.

The operating pedal 14 also includes two pairs of motion sensors, such as the four micro-switches 42 (operated by movement of the foot pad 28), a micro-controller 38, and a motor interface 40 which interface generates power signals for the motor of the injection device 12.

Figure 5:
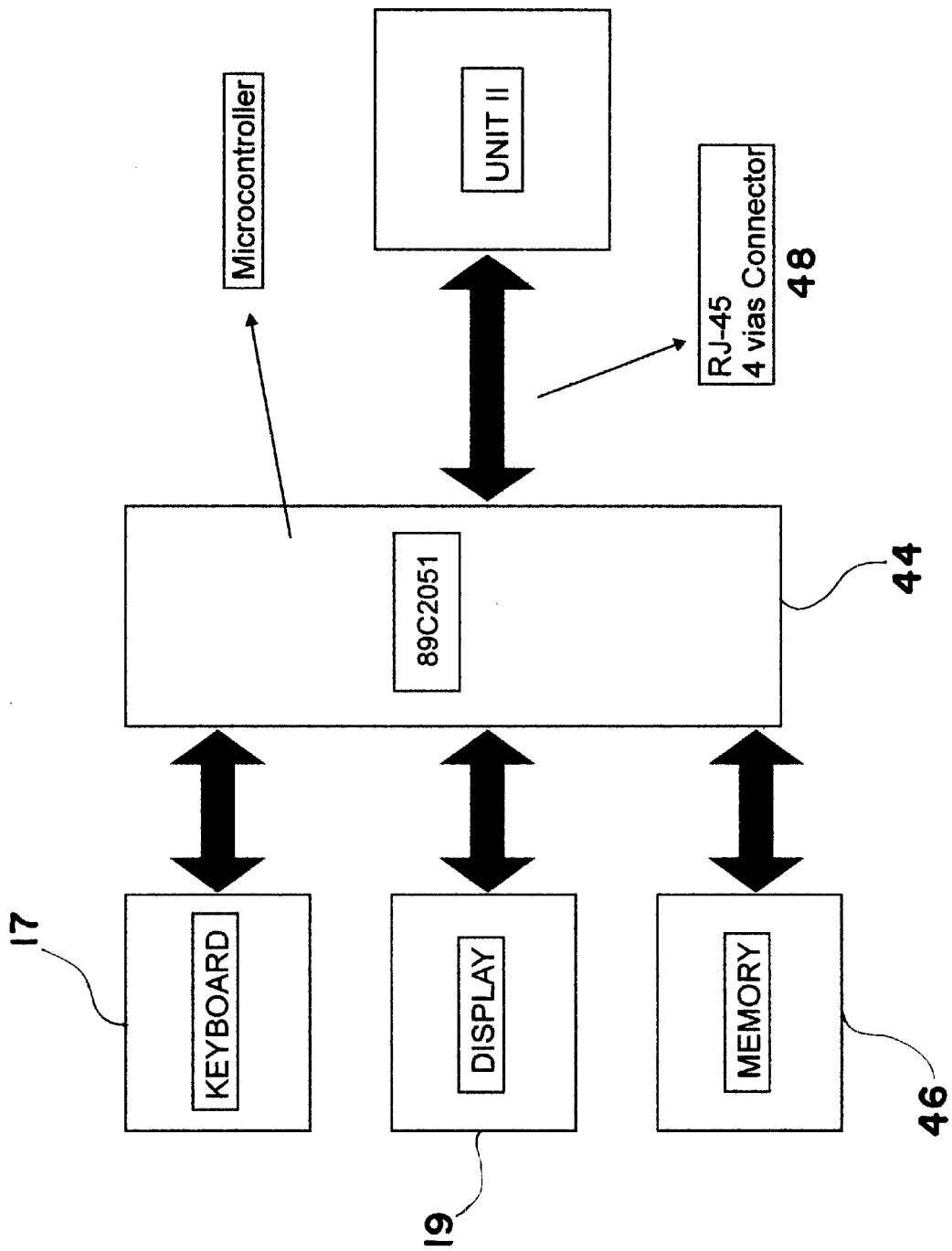
FIG. 5 is a block diagram of the components of the control unit of the injection device of FIG. 1.

Referring to FIG. 5, the control unit 16 includes a microcontroller 44, the keyboard 17, the display 19, a memory 46 for semi-permanent storage of procedures and for temporary storage of current operating parameters (e.g., volume of liquid dispensed during a current procedure), and a connection port 48 for receiving power and for transmitting and receiving signals to and from the operating pedal 14.

The liquid injection system 10 provides a number of modes of operation including: a Preparation mode, which calibrates the injector for the particular liquid cartridge to be used; an Introduction mode, which provides a low-rate, intermittent i dose of anesthetic for painless insertion of the needle; an Injection mode, which provides a steady, programmable flow rate for delivering the anesthetic to the desired location; an Aspiration mode which slightly retracts the hollow piston 128, pauses and then returns the hollow piston 128 to its original position to allow visual inspection of the withdrawn liquid; and a Programming mode whereby a user can store injection procedures in the memory of the control unit 16. The Preparation, Introduction and Aspiration modes are pre-programmed in the memory of the control unit 16 and preferably cannot be altered by the user. The control unit 16 also preferably includes a number of pre-programmed injection procedures select the keyboard 17 of the control unit 16, which also cannot be altered.

The Preparation mode is required because the location of the rubber stopper, or bung, in the cartridge (see FIGS. 6 and 7) can vary depending on the manufacturer and type of cartridge. When the Preparation mode is activated, the motor 20 of the injector device 12 is activated to advance the hollow piston 128 at a speed which would correspond to a liquid flow rate of about 0.3 ml/min. When the operator observes a first drop of anesthetic forming at the end of the needle of the injector 12, the Preparation mode is ceased. During the Preparation mode, the control unit 16 does not increment the value corresponding to the volume amount of liquid expelled from the cartridge. Thus, upon completion of the Preparation mode, the injection device 12 is properly calibrated for the currently installed anesthetic cartridge.

The Preparation mode is preferably initiated by depressing the foot pad 28 of the operating pedal 14 to the side (e.g., the right side), and holding the foot pad 28 down until the first drop of liquid is observed on the tip of the needle, and then releasing the foot pad 28. Preferably, to initiate the Preparation mode, the hollow piston 128 of the injection device 12 must be in a fully retracted, or "zero" position, which can be achieved by depressing a Restart key on the control unit 16 or by cycling the On/Off switch of the operating pedal 14. This will prevent unintended or accidental initiation of the Preparation procedure.

The Introduction mode provides a pre-programmed, timed, alternating flow rate, suitable for inserting the needle. It is intended that, during the higher of the two flow rates, the user will advance the needle toward the intended destination, and that during the lower of the two flow rates, the user will cease advancing the needle to allow the anesthetic to anesthetize the area immediately preceding the needle, thereby providing for painless insertion of the needle. The higher of the two flow rates is preferably about 0.15 ml/min, and has a duration of about 5 seconds. This is immediately followed by the lower of the two flow rates, which is preferably about 0.075 ml/min, with a duration of about 2.5 seconds. This sequence repeats for the duration of the introduction procedure allowing the medical liquid to penetrate the tissue surrounding the needle (including hard tissues) without stressing the nerves, thus avoiding the pain from the insertion of the needle.

During the period corresponding to the low flow rate in the Introduction mode, the control unit 16 preferably emits a sonorous signal and displays a warning message, such as "Stop the. Needle", to indicate that the user should cease advancing the needle. The Introduction mode is preferably initiated by depressing the foot pad 28 of the operating pedal 14 backward (e.g., by the heel).

The Injection mode is the mode wherein the anesthetic is delivered to the intended destination. The injection system 10 provides for programmable injection flow rates of about 0.3 ml/min to 1.0 ml/min, in about 0.05 ml/min increments, and for programmable total injection volumes of about 0.1 ml to about 1.8 ml, in about 0.1 ml increments. During activation of the Injection mode, the control unit 16 preferably emits a sound after about every 0.1 ml is expelled from the needle, or another predetermined amount. Upon completion of the pre-programmed injection volume, a different sound is emitted and the control unit 16 displays a message, such as "Final Dose", indicating the completion of the injection procedure. The injection procedure can be interrupted and resumed by releasing, and then depressing, respectively, the foot pad 28 of the operating pedal 14. Thus, the user has complete control over the injection procedure.

In a fully operative mode of the injection system 10, all three components of the injection system 10 (i.e., the injection device 12, operating pedal 14 and control unit 16) are used. The desired injection procedure (either pre-programmed or entered manually immediately prior to the procedure) is selected using the keyboard 17 of the control unit 16, and, once selected, the procedure is initiated by depressing the foot pad 28 of the operating pedal 14, preferably frontwards, thereby activating the Injection mode.

In a limited operation mode of the injection system 10, only the injection device 12 and the operating pedal 14 are used. The limited Injection mode can be activated by depressing the foot pad 28 preferably frontward (to deliver a pre-programmed, fixed-rate injection flow of 0.3 ml/min), or to the right (for a pre-programmed, fixed-rate injection flow of 1.0 ml/min). Thus, the limited Injection mode provides two fixed alternative injection speeds.

The Aspiration mode is used to prevent accidental intravenous injection of anesthetic. In the Aspiration mode, the motor 20 of the injection device 12 operates in reverse for a short period to withdraw the hollow piston 128 a short distance to withdraw a maximum of about 0.2 ml of fluid in about 1.33 seconds. The motor 20 then pauses for about 1 second to allow visual inspection of the withdrawn liquid for blood, and then operates in a forward direction to return the hollow piston 128 to its original position, again in about 1.33 seconds. The Aspiration mode is preferably activated by a relatively quick depression of the foot pad 28 of the operating pedal 14 to, for example, the left. During the Aspiration mode, which can last for approximately 3.66 sec, the operating pedal 14 remains inactive and the control unit 16 displays a message, such as "Stop the needle", to instruct the user to cease advancing the needle. The aspiration mode can preferably be activated during an intermission of either an Introduction or Injection procedure.

In the Programming mode, the control unit 16 is used to enter the desired injection flow rate and the desired injection volume (i.e., the dosage). For example, in the Programming mode, the up/down keys of the keyboard of the control unit 16 are used to select an Injection Rate item. Then the left/right keys are used to select an injection rate value from a list of 15 available rates. The Confirm key is used to store the selection. The desired injection volume is selected in a similar manner by selecting an Injection Volume item and then an injection volume value from a list of 18 available volumes. Upon selection and storage of the desire rate and volume, the injection procedure (and the other procedures) are initiated with the operating pedal 14.

In an automatic mode, the desired injection procedure is selected by number, from a database of pre-programmed procedures stored in the memory of the control unit 16. Preferably, a plurality of injection procedures are permanently stored in the control unit 16 such the injection rates and volumes cannot be altered or lost. In this manner, a user can become familiar with, and can rely on the accuracy and integrity of the fixed procedures.

For example the following six (6) injection procedures can be permanently recorded in the memory of the control unit 16: (1) The Advanced Subperiosteal Anesthetic Technique (ASAT), for the anterior region of the maxilla, including the canine teeth (rate 0.3 ml/min, volume 0.3 ml); (2) the Advanced Subperiosteal Anesthetic Technique (ASAT), for the anterior region of the mandible and the posterior region of the maxilla, including the pre-molars and molars (rate 0.3 ml/min, volume 0.6 ml); (3) the Spongy Ossy Zone/Alveolar Crest (CAZOE), for the molars of the mandible (rate 0.3 ml/min, volume 0.9 ml); (4) Spongy Ossy Zone/Alveolar Crest (CAZOE), for the molars (rate 0.3 ml/min, volume 1.2 ml); (5) Palatine Injection, for anterior/posterior nerve block, as well as to complement any molar anesthesia at the palatal root (rate 0.3 ml/min, volume 0.3 ml); and (6) Convention Technique, for supraperiosteal, inferior alveolar nerve blocks and others (rate 1.0 ml/min, volume 1.8 ml).

A particular pre-programmed injection procedure is selected using the keyboard 17 of the control unit 16, such as the up/down keys, and is initiated with the operating pedal 14. A user can record additional procedures by using the left/right keys of the keyboard 17 to select an available procedure number (e.g. 7), then, using a combination of the up/down and the and left/right keys, enter and Confirm: (1) a name for the new procedure, (2) the desire flow rate, and (3) the dosage volume.

Figure 6:
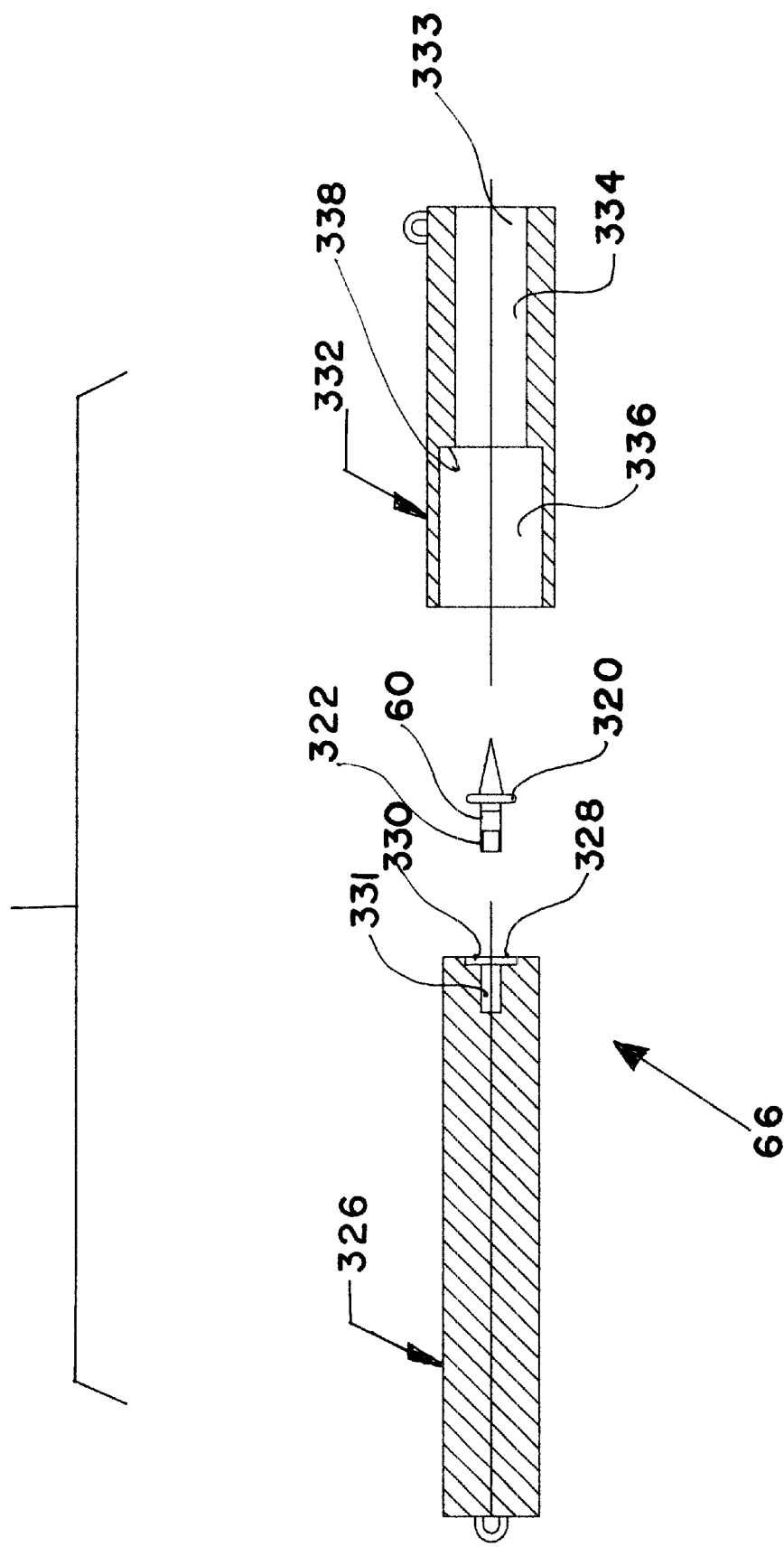
FIG. 6 is an exploded view of the harpoon/cartridge assembly device.
Figure 7:
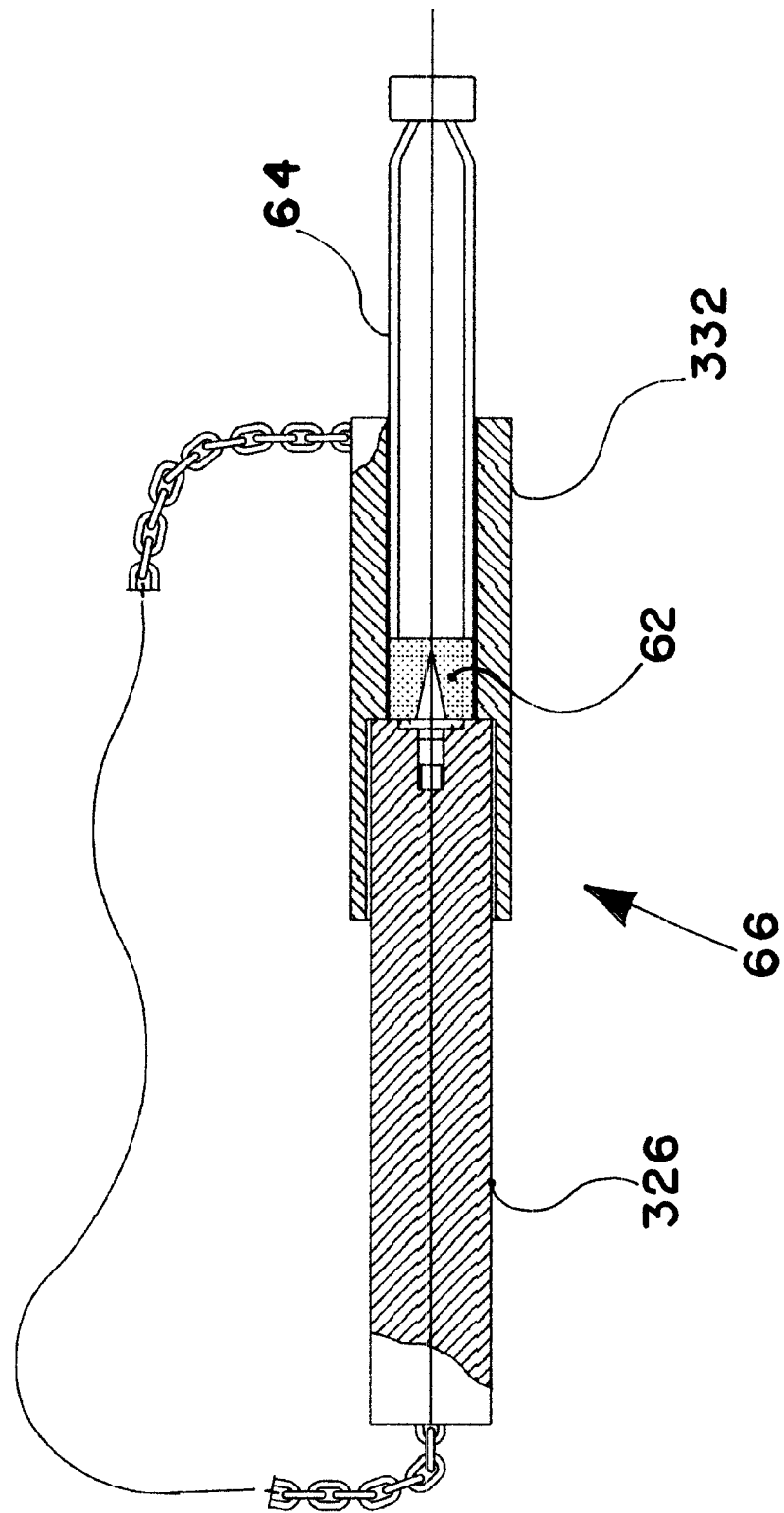
FIG. 7 is an assembly view of the harpoon/cartridge device of FIG. 6.

Referring to FIGS. 6–7, a harpoon/cartridge assembly device 66 is used to ensure that the harpoon 60 is properly seated in the rubber stopper 62 (i.e., the bung) of the cartridge 64. As best seen in FIG. 8A, the harpoon 60 has a conical portion 318 having threads (not shown), a collar 320, and a shaft 322, which has a cross section which is generally non-circular. An outer portion 324 of the shaft 322, which is spaced a distance from the collar 320 is threaded and has a partially circular cross section. An inner portion 325 of the shaft 322 is not threaded and has a maximum diameter (measured from the center of curvature of the threads) less than that of the minimum diameter of the outer threaded portion thereof.

Referring again to FIGS. 6–7, the harpoon/cartridge assembly device 66 includes a harpoon seat 326 having a recess 328. The recess 328 has an outer portion 330 with a depth and cross section corresponding to that of the collar 320 of the harpoon. The recess 328 also has an interior portion 331 which is sized and shaped to closely receive the non-circular shaft 322 of the harpoon 60.

The harpoon/cartridge assembly device 66 also includes a cartridge support 332 which has a through opening 333 having a first portion 334 sized and shaped to closely receive a cartridge 64, and a second portion 336, sized and shaped to closely receive the end of the harpoon seat 326 having the recess 328. The diameter of the harpoon seat 326 and the second portion 336 of the through opening 333 of the cartridge support 332 is larger than the diameter of the first portion 334 of the through opening 333. Therefore, the inward movement of the harpoon seat 326 (and the harpoon 60 seated therein) is limited by the wall 338 between the first and second portions 334, 336 of the through opening. The inward movement of a cartridge 64 is limited by the harpoon seat 326. Preferably, the harpoon seat 326 and the cartridge support 332 are connected by a leash, as shown.

To mount the harpoon 60 to the cartridge 64, the following steps are taken:

(1) The harpoon 60 is seated in the harpoon seat 326, (2) the harpoon seat 326 is inserted into the cartridge support 332 through the first portion 334 of the through opening 333, until the harpoon seat 326 abuts the wall 338, (3) the cartridge 64 is inserted into the cartridge support 332 through the second portion 336 of the through opening 333, until the rubber stopper 62 contacts the threaded conical portion 318 of the harpoon 60, and then (4) the cartridge 64 is rotated together relative to the harpoon seat 324 and urged into the cartridge support 326 to thread the rubber stopper onto the harpoon 60. When the rubber stopper 62 is fully threaded onto the harpoon 60, the collar 320 contacts the rubber stopper 62, preventing further movement. Then the cartridge 64 and harpoon 60 are withdrawn from the cartridge support 326 and are ready to mount to the injector 12.

Figure 8:
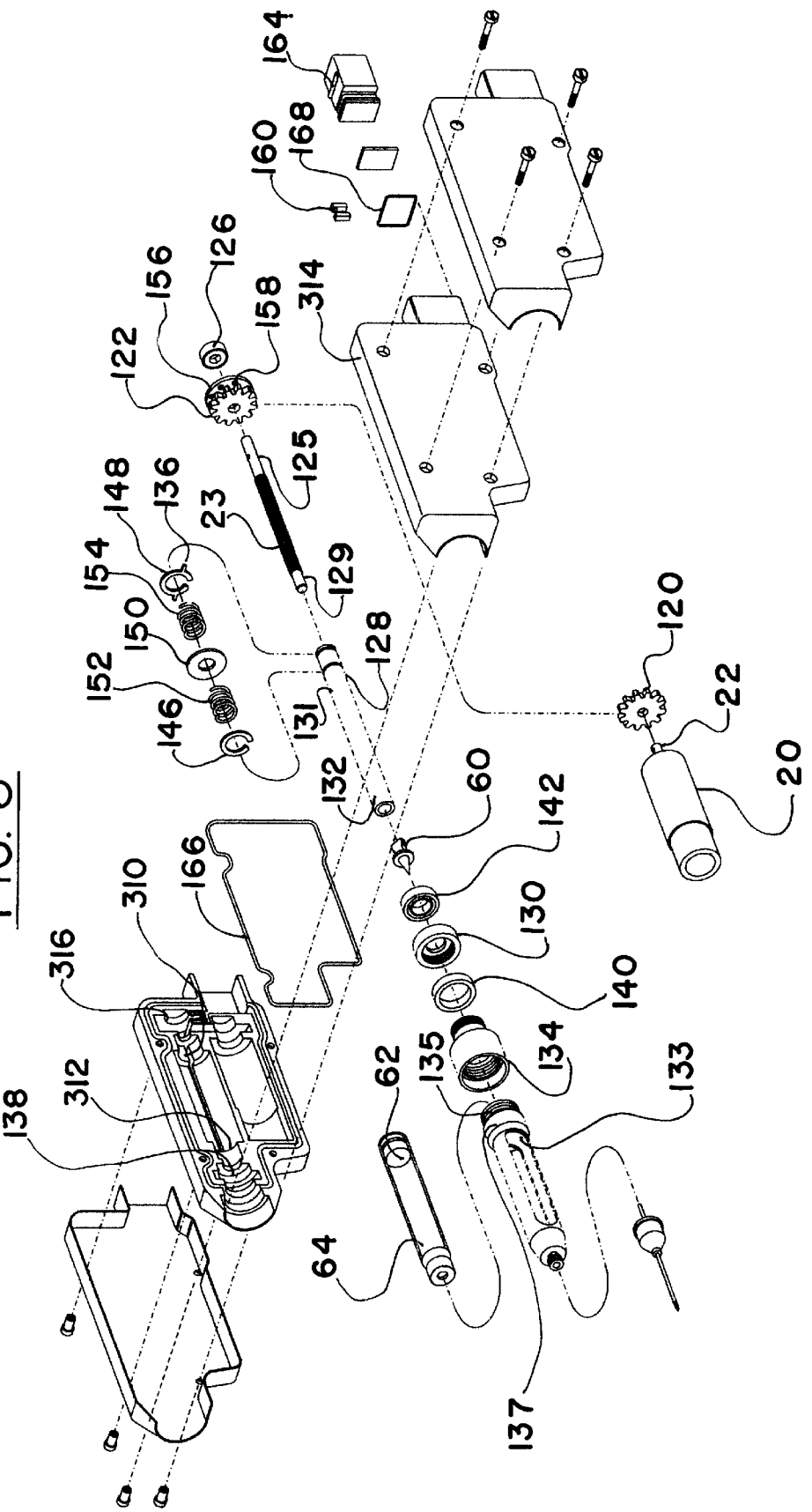
FIG. 8 is an exploded view of the injection device.
Figure 9:
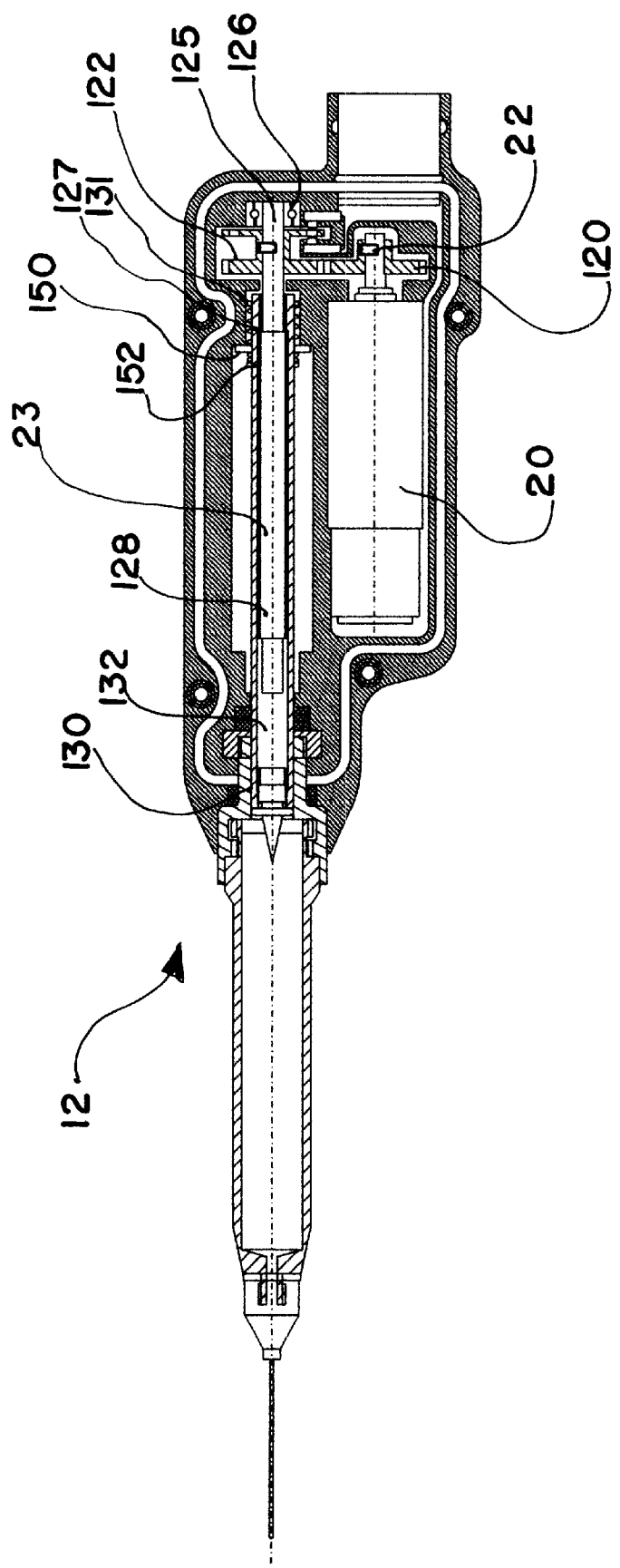
FIG. 9 is a cross-sectional, elevational view of the injection device of FIG. 8.

Referring to FIGS. 8 and 9, the precision injector 12 is a small, pen-like device suitable for operation with one hand. The injector 12 includes the motor 20, and first and second spur gears 120, 122. The first spur gear 120 is connected to a drive shaft 22 of the motor 20 and the second spur gear 122 is connected to a threaded shaft 23 aligned directly above and parallel to an axis of rotation of the drive shaft 22 of the motor 20. A proximal end 125 of the threaded shaft 23 adjacent the second spur gear 122 is supported by a bearing 126. A hollow piston 128, with an internal thread is threaded over the threaded shaft 23. A distal end 132 of the hollow piston 128, opposite the bearing 126, is supported by a bushing 130. Thus, it can be appreciated that, rotation of the motor 20 will cause the hollow piston 128 to move frontward or backward according to the direction of rotation of the motor 20 (clockwise or counter-clockwise), and that the hollow piston 128 will travel at a velocity proportional to the rotational speed of the motor 20, establishing the injection rate.

The hollow piston 128 is threaded internally, along a relatively short length adjacent the proximal end 131 thereof. Thus, when the threaded portion 127 of the hollow piston 128 travels beyond the threads of the threaded shaft 23, the threaded portion 127 of the hollow shaft 128 becomes disengaged from the thread of the threaded shaft 23.

The proximal and distal ends 125, 129 of the threaded shaft 23 include areas of reduced cross section which lack threading to prevent over-travel of the hollow piston 128. To re-engage the threads of the threaded shaft 23, the hollow piston 128 includes a clutch assembly comprised of two spaced-apart c-clips 146, 148 mounted within circular channels in the hollow piston 128. Between the c-clips 146, 148 is a washer 150 intermediate two springs 152, 154. The washer contacts wall portions 310, 312 of the shells 314, 316 of the injector device 12 when the hollow piston 128 is in the forwardmost or rearmost overtravel positions, respectively. When the hollow piston is in rearward overtravel position (as in FIG. 9), the washer 150 compresses the forward spring 152 which urges the hollow piston 128 forward such that the threaded portion 127 thereof contacts the thread of the threaded shaft 23. The clutch assembly works in a complementary manner in the case of forward overtravel. Thus, it can be appreciated that the clutch assembly serves to maintain the end threads 127 of the hollow piston 128 in contact with end threads of the threaded shaft 23 when the threads disengage such that, upon a change of direction of the motor 20, the threads re-engage.

To prevent the hollow piston 128 from rotating along with the threaded shaft 23, one of the c-clips 146 or 148 includes outwardly extending wing portions 136 (see FIG. 8) which engage channels (not shown) in the shell halves 314, 316 of the injector device 12. In addition, the circular channel in the hollow piston 128 in which the one C-clip 146 or 148 is mounted is not complete and therefore prevents the hollow piston 128 from turning relative to the C-clip, and the threaded shaft 23. Therefore, it can be appreciated that upon rotation of the threaded shaft 23, the hollow piston 128 must translate forward or backward.

As described above, the harpoon 60 is threaded into the rubber stopper 62 of the medical liquid cartridge 64 using the harpoon/cartridge assembly device 66. The cartridge/harpoon assembly is then inserted within a cartridge case 133 which is then connected to the body of the injector 12. The cartridge case 133 includes threads 135 on a proximal end 137 thereof which engage a threaded connector 134 threaded to the bushing 130. The bushing 130 is fixedly located within a cavity 138 formed in the body of the injector 12 by the left and right shells 314, 316. A sealing ring 140 is located between the threaded connector 134 and the threaded bushing 130, and jointing material 142 is located adjacent the bushing 130, opposite the sealing ring 140.

Figure 14:
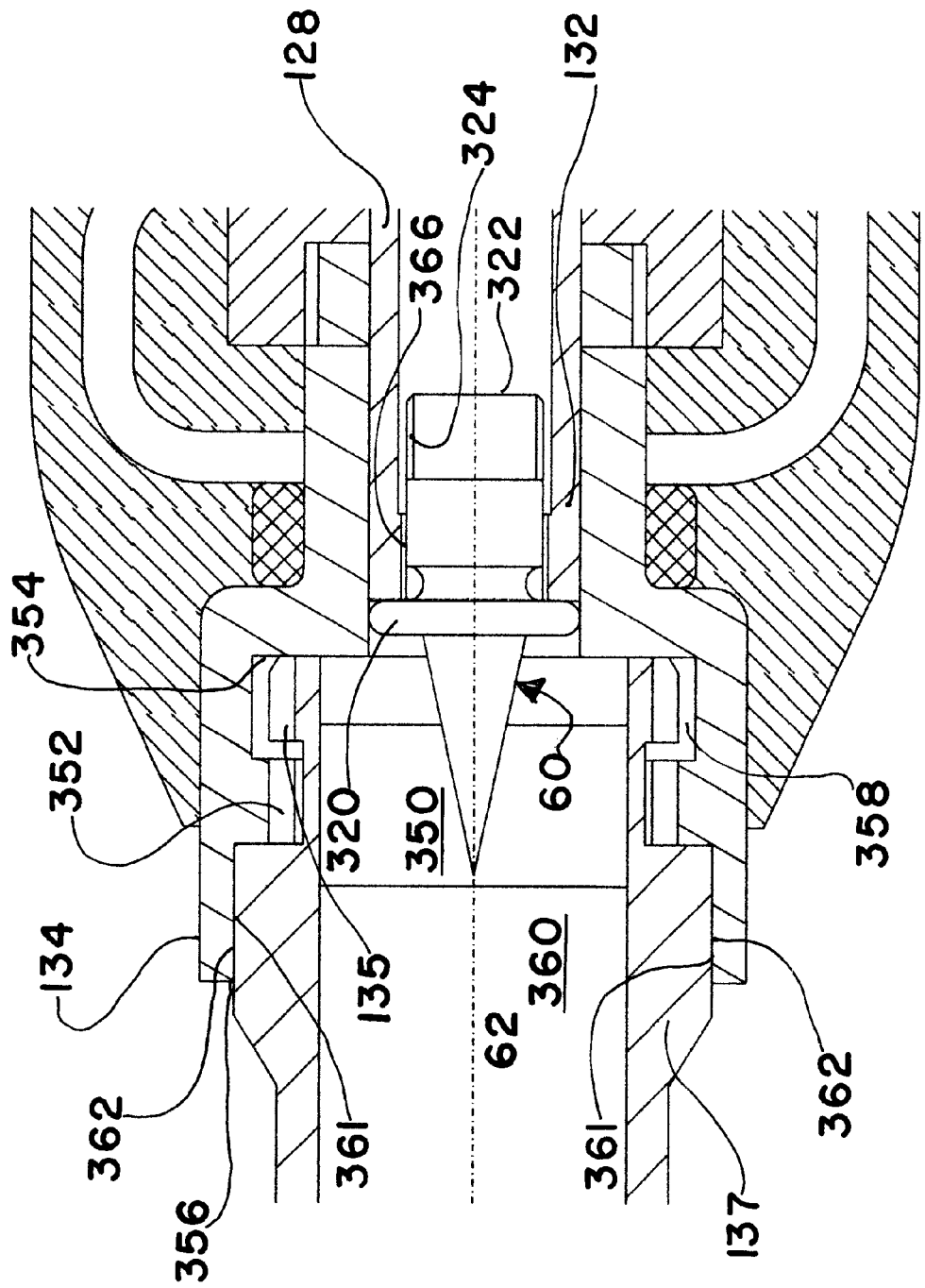
FIG. 14 is a side elevational, close-up view of the injection device showing the means to permit free rotation of the cartridge case, cartridge and needle with respect to the body of the injection device.

As best seen in FIG. 14, the threaded connector 134 forms a cavity 350 for receiving the proximal end 137 of the cartridge case 133. The cavity 350 includes an internally threaded portion 352 intermediate a bottom wall 354 and an opening 356 of the cavity 350. The threaded portion 352 is dimensioned to engage the threads 135 of the cartridge case and generally divides the cavity 350 into inner and outer portions 358, 360; the inner portion being bounded by the bottom wall 354 and the threaded portion 352, and the outer portion being bounded by the threaded portion 352 and the opening 356. The distance between the bottom wall 354 and the threaded portion 352 is greater than the width of the threaded portion 135 of the cartridge case 133, and the diameter of the inner portion 358 of the cavity 350 is greater than the maximum diameter of the threads 135 of the cartridge case 133. Thus, when the cartridge case 133 is fully threaded into the threaded connector 134, the threads 135 of the cartridge case 133 pass beyond the threaded portion 352 of the threaded connector 134 and into the inner portion 358 of the cavity 350, which allows the cartridge case 133 to rotate freely with respect to the body of the injector 12. However, in this position the cartridge case 133 is trapped between the threaded portion 352 and bottom wall 354 of the threaded connector 134.

Walls 361 of the outer portion 360 of the cavity 350 of the threaded connector 134 closely receive an outer wall 362 of the cartridge case 133 to stabilize the cartridge case 133 in the fully installed position.

The distal end 132 of the hollow piston 128 includes an internal thread 366 dimensioned to engage the threaded portion 324 of the harpoon 60. The internal thread 366 of the distal end 132 of the hollow piston 128 has a length less than a distance between the collar 320 and the threaded portion 324 of the harpoon 60, and less than or equal to the length of the threaded portion 352 of the threaded connector 134. Also, the internal diameter of the thread 366 of the hollow piston 128 is greater than a maximum diameter of shaft 322 of the harpoon 60 between the collar 320 and the threaded portion 324 of the harpoon 60. Thus, when the cartridge case 133 (and cartridge/harpoon assembly) is fully threaded into the threaded connector 134, the threaded portion 324 of the harpoon 60 will be fully threaded past the thread 366 of the hollow piston 128; and the cartridge case 133 and the cartridge/harpoon assembly can rotate freely with respect to the body of the injector 12. This allows free angular (i.e., rotational) orientation of the needle 18 (which preferably has an inclined tip), without altering the orientation of the entire injector 12.

It can be appreciated that when the hollow piston 128 is extended from the position shown in FIG. 14 (e.g., during the Injection Mode), the distal end 132 of the hollow piston 128 will contact the collar 320 of the harpoon 60, thus exerting an outward force on the rubber stopper 62 of the cartridge 64. This force will urge the cartridge 64 and cartridge case 133 outward until the threads 135 of the cartridge case 133 abut the threads 352 of the threaded connector 134, which prevents further outward movement of the cartridge case 133. Additional extension of the hollow piston 128 will cause the rubber stopper 62 of the cartridge 64 to plunge into the cartridge 64 thereby expelling the liquid therein. Similarly, when the hollow piston 128 is withdrawn (e.g., during the Aspiration Mode), the threads 366 of the hollow piston 128 abut the threads 324 of the harpoon 60 thereby exerting an inward force on the harpoon 60. Since the harpoon 60 is firmly threaded into the rubber stopper 62, this causes the rubber stopper to be withdrawn resulting in a withdrawal of liquid into the cartridge 64.

Referring again to FIG. 8, the injector 12 includes a ring 156 fixedly connected to the threaded shaft 23, which ring 156 has a plurality of holes 158 preferably 8. As shown, the ring 156 can be integrally formed with the second spur gear 122. Aligned on opposite sides of the holes 158 is an optical reader 160 which generates a pulse upon the passage of one of the holes. The signal from the optical reader 160 is transmitted to the control unit 16 for monitoring and adjusting the speed and duration of operation of the motor 20.

The injector 12 includes sealing material to prevent the ingress of water and contaminants. A first sealing material 166 is located between the left and right shells 314,316. The sealing ring 140 is located between the threaded connector 134 and the threaded bushing 130. Another sealing material 168 is located around the cable connection port 164. Thus, the internal components of the injector are hermetically sealed. This provides that the injector 12 can be cleaned and sterilized in the convention manner, such as with an autoclave.

The external shells 314, 316 of the injector 12 are preferably formed from injection molded polypropylene and, when assembled, have dimensions of preferably about 116 mm×40 mm×18 mm. The motor 20 is preferably a high precision motor such as motor model 1319S Micro motor, available from Mini Motors AS, CH-6980 Croglio, Switzerland.

Referring to FIGS. 10–13, the operating pedal 14 includes a lower casing 200 which houses a ball joint 202 seated in a cavity 204. The ball joint 202 is rotatably secured to the lower casing 200 by a ball joint support 206. A movable cross arm 208 is fixed to the ball joint 202 above and through the ball joint support 206 and extends upwardly through a cover 210 fixed to the lower casing 200. The cover 210 includes a cross-shaped opening 212 sized and shaped to allow the passage of the movable cross arm 208 therethrough. A foot pad 28, which includes an arched, upwardly-extending heel registration flange 216 is fixedly connected to the movable cross arm 208 for engagement by the foot of the operator.

Microswitches 42, such as the electromechanical microswitches shown, are located below each arm 220 of the movable cross arm 208. Thus, the microswitches 42 can be activated by rotating the foot pad 28 with respect to the casing 200. Springs 218 located below each arm 220 bias the cross arm 208 and foot pad 28 in a horizontal or neutral position.

The operating pedal 14 also includes two cable connector ports 34, 36 (preferably RJ-45 modular connectors), a power switch 32, a fuse 33, 110V/220V voltage selector switch 37, a power connector 41 and a transformer 39. The transformer 39 preferably provides power for all the components of the injection system 10, the power being transmitted to the injection device 12 and the control unit 16 via the cables.

Figure 4:
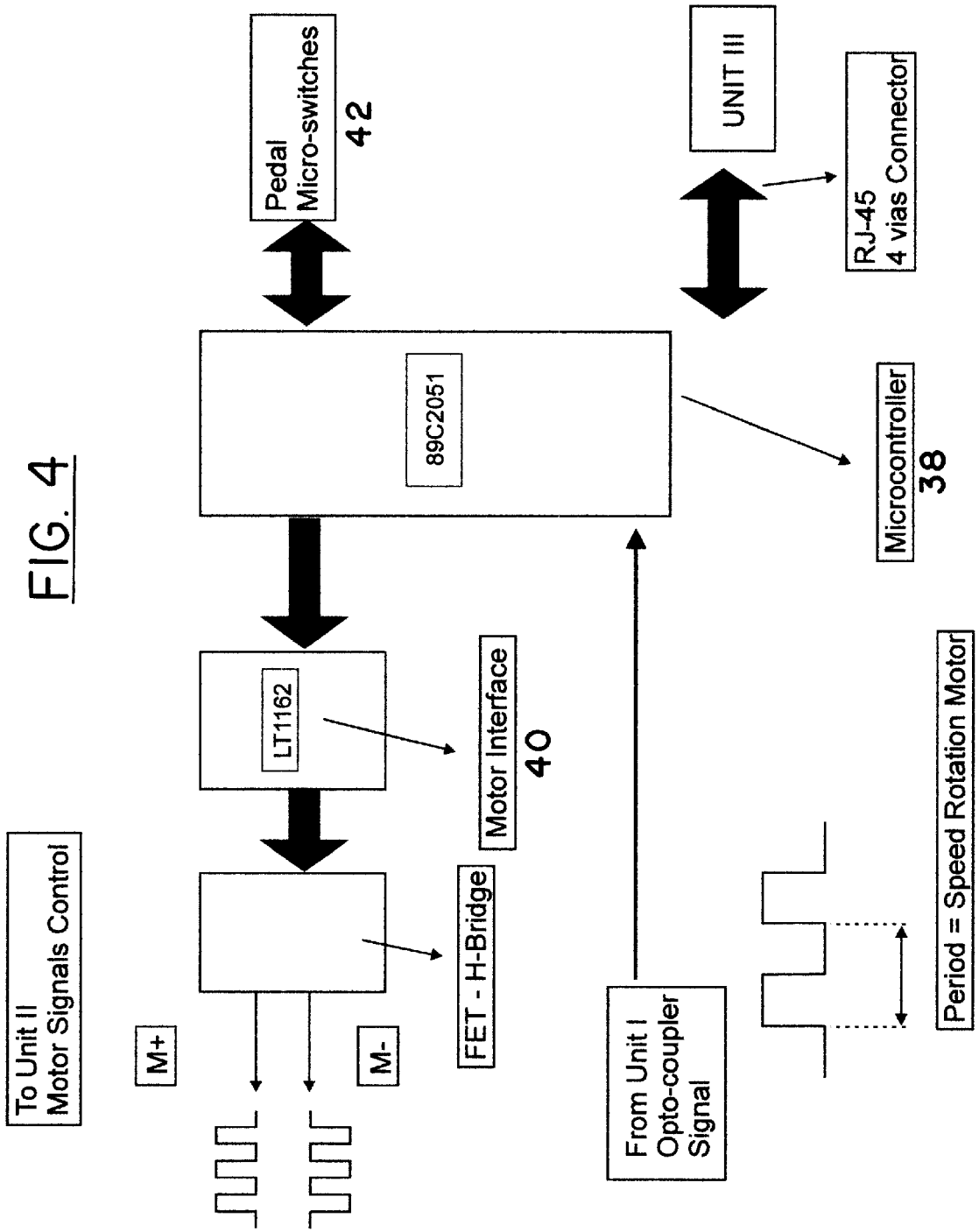
FIG. 4 is a schematic diagram of the control unit of the injection device of FIG. 1.
Figure 10:
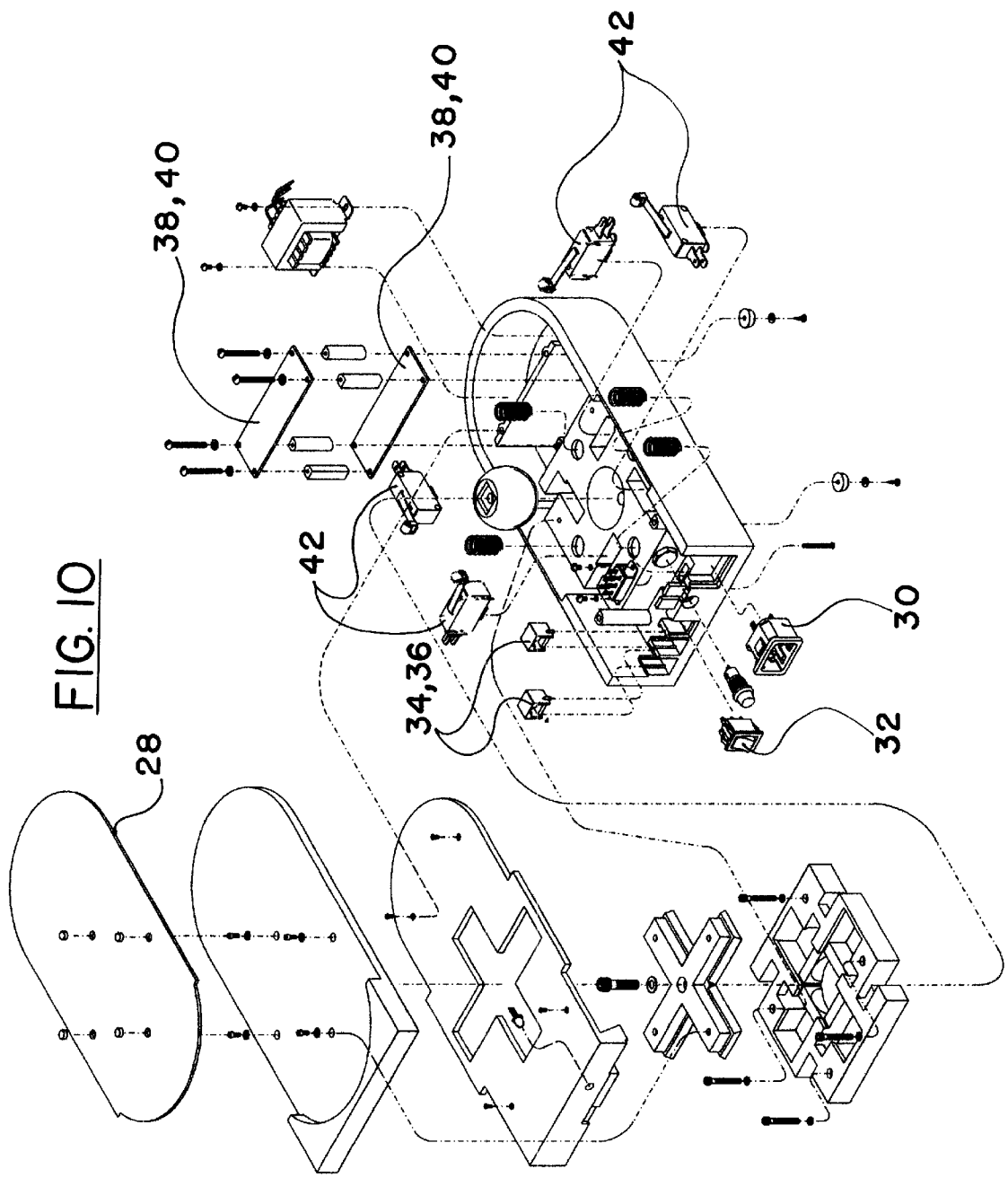
FIG. 10 is an exploded view of the operating pedal.
Figure 11:
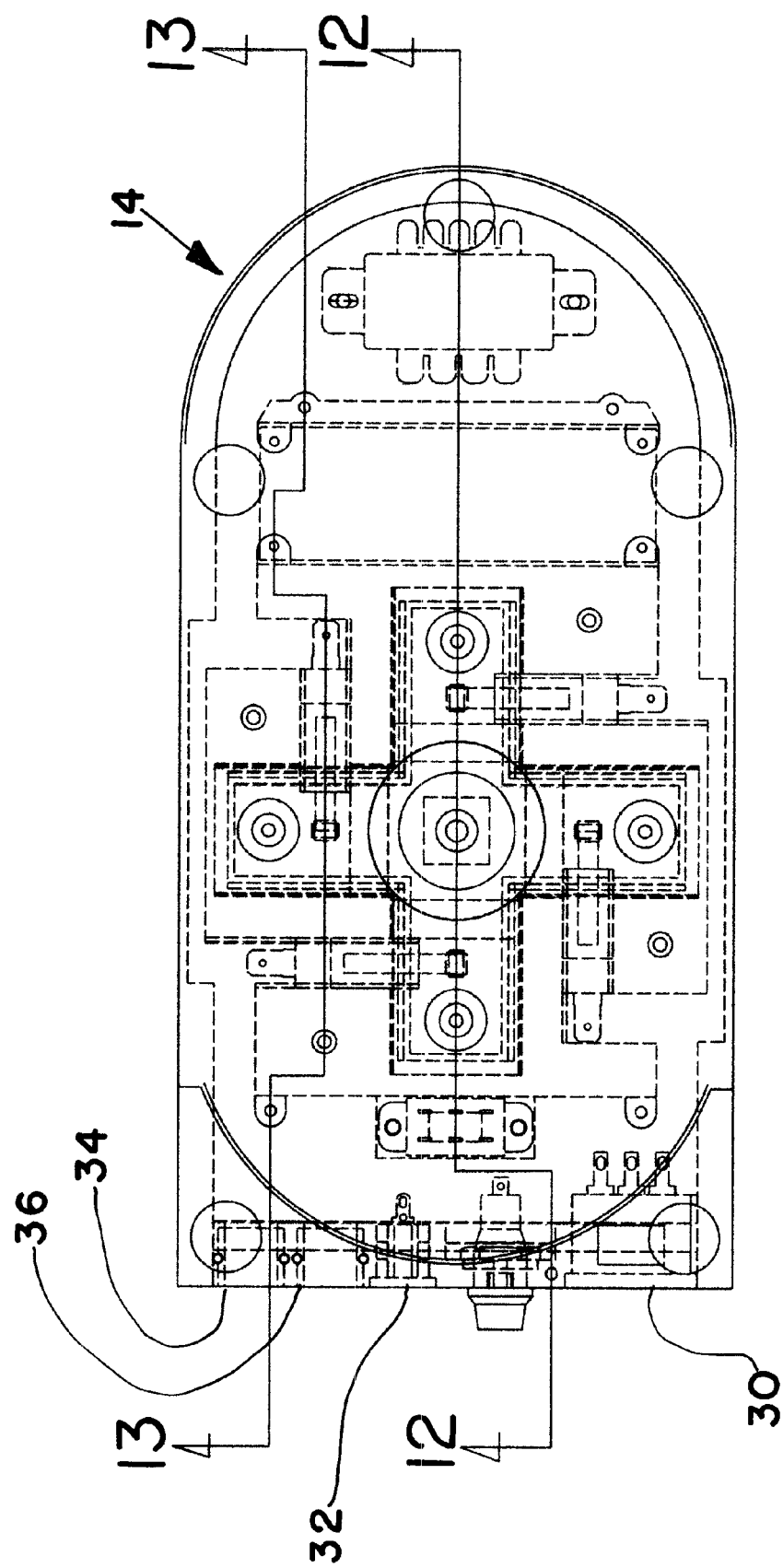
FIG. 11 is a top, plan view of the operating pedal of FIG. 10.
Figure 12:
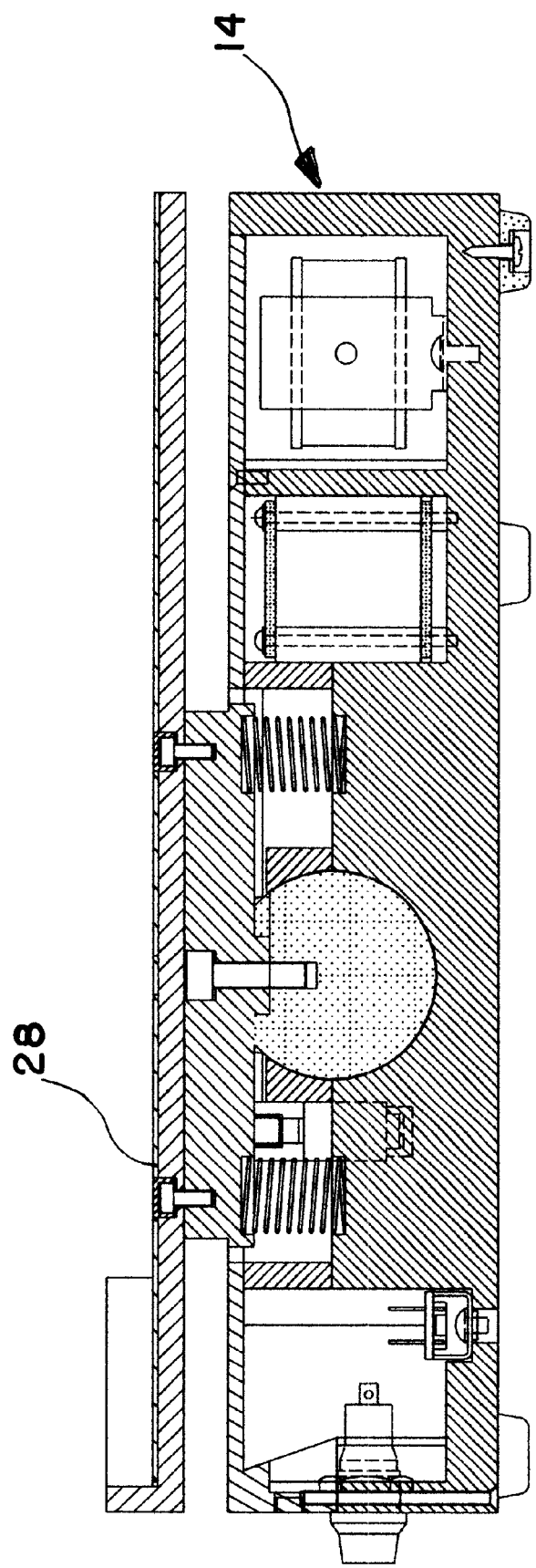
FIG. 12 is a side elevational view of the operating pedal, taken along line 12—12 of FIG. 11.
Figure 13:
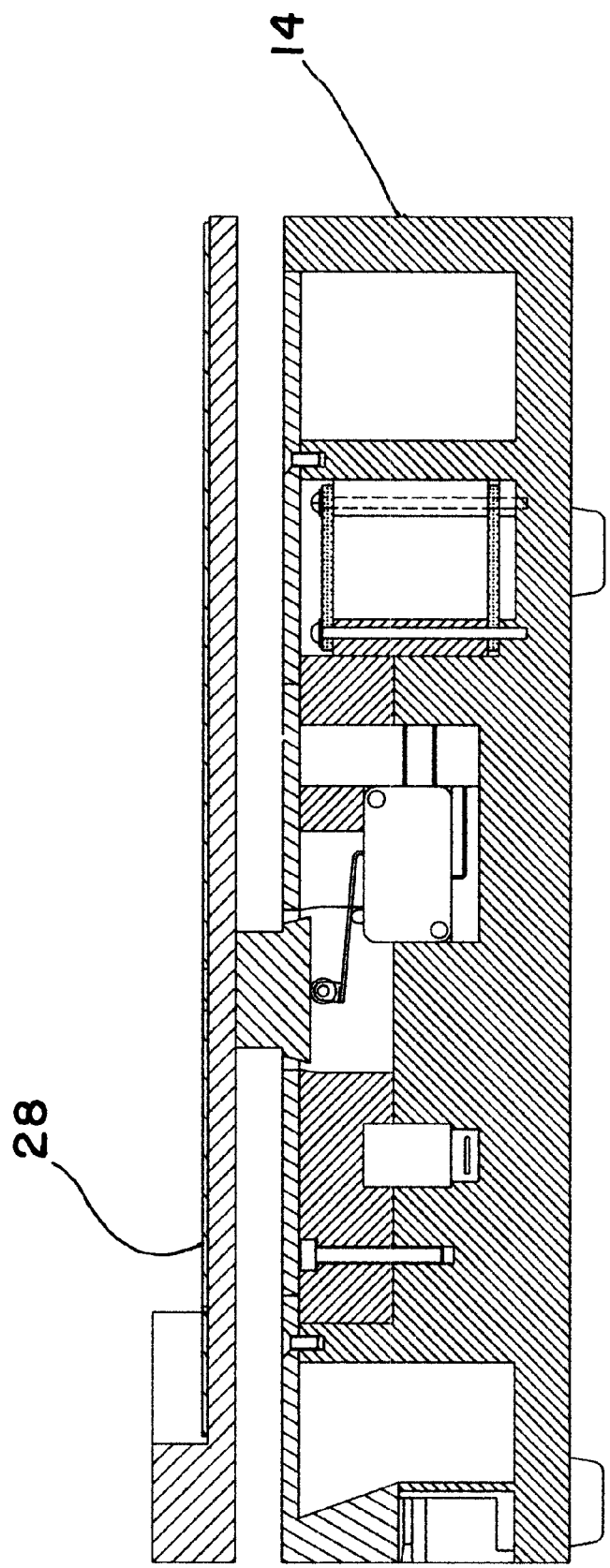
FIG. 13 is a side elevational view of the operating pedal, taken along line 13—13 of FIG. 11.

Referring to FIGS. 4 and 10, the electronic circuits 232, 234 in the operating pedal 14 receive a signal from the optical reader 160 in the injection device 12 to measure and monitor the actual rotational speed of the shaft 23 of the injection device 12. As a result of the analysis of the signal, software-based PWM (i.e., Pulse With Modulation) is applied to a power circuit of the motor interface 40 which feeds power to the motor 20 until the motor reaches the correct rotational speed. The circuit also stops and drives the motor in both directions using a FET H-Bridge output stage.

It should be understood, of course, that the specific form of the invention herein illustrated and described is intended to be representative only, as certain changes may be made therein without departing from the clear teachings of the disclosure. Accordingly, reference should be made to the following appended claims in determining the full scope of the invention.

I claim:

1. A medical liquid injection system, comprising:
    a hand-held injection device having a motor, a cartridge case for holding a medical liquid cartridge, a needle, and means, connected to said motor, for expelling liquid from said cartridge through said needle;
    a foot-operable pedal connected to said injection device for controlling the operation of said motor;
    a control unit connected to said foot-operable pedal for selecting or programming injection procedures;
    said injection system having a preparation mode for calibration of said cartridge, an introduction mode for advancing said needle to a desired location, an aspiration mode for detecting and preventing intravenous injection of the medical liquid, and an injection mode for delivering the medical liquid to the desired location;
    said preparation, introduction, aspiration, and injection modes being independently selectable by depressing said foot-operated pedal in discrete directions. operable during a continuous depression of said foot-operable pedal in a predetermined direction and ceasing upon release of said foot-operable pedal.

2. A medical liquid injection system as in claim 1, wherein during said preparation, introduction, aspiration and injection modes, said control unit displays a textual or graphical current mode message indicating to the user the current mode in operation.

3. A medical liquid injection system as in claim 1, wherein, in said preparation mode, said motor operates in a direction to expel liquid from said cartridge at a predetermined relatively low flow rate, said preparation mode being operable during a continuous depression of said foot-operable pedal in a predetermined direction and ceasing upon release of said foot-operable pedal.

4. A medical liquid injection system as in claim 1, wherein in said introduction mode:
    said motor operates in a direction to expel liquid from said cartridge;
    said motor operates at a first, relatively high rate, for a first predetermined period of time and operates at a second, relative d predetermined period of time;
    said control unit emits a sonorous signal during said operation of said motor at said second rate;
    said motion alternates between said first and second rates for the duration of the introduction mode to deliver an optimal amount of the medical liquid at an optimal rate thereby allowing the liquid to penetrate the tissue surrounding the needle without stressing the nerves, to avoid pain without causing undesirable numbness, or over dosage.

5. A medical liquid injection system as in claim 4, wherein during operation of said motor at said second rate during said introduction mode, said control unit displays a warning message suitable to direct the user to cease advancing said needle.

6. A medical liquid injection system as in claim 4, wherein said introduction mode continues during depression of said foot-operable pedal in a predetermined direction and ceases upon release of said foot-operable pedal.

7. A medical liquid injection system as in claim 1, wherein, in said aspiration mode:
    said motor operates in a direction to withdraw a predetermined amount of liquid into said cartridge, at a relatively low rate, pauses for a predetermined period, and then operates in an opposite direction, to expel an amount of liquid from said cartridge equal to said predetermined amount withdrawn, so the injection process can be continued.

8. A medical liquid injection system as in claim 7, wherein said aspiration mode is activated by transient depression of said foot-operable pedal in a predetermined direction.

9. A medical liquid injection system as in claim 8, wherein said foot-operable pedal need not be operated for the duration of said aspiration mode.

10. A medical liquid injection system as in claim 7, wherein, during said aspiration mode, said control unit emits a sonorous warning signal.

11. A medical liquid injection system as in claim 10, wherein, during said aspiration mode, said control unit displays a warning message suitable to direct the user to cease advancing the needle.

12. A medical liquid injection system as in claim 1, wherein, in said injection mode, said motor operates in a direction to expel liquid from said cartridge and said control unit emits a sonorous signal after each of a predetermined volume of liquid is ejected from said cartridge.

13. A medical liquid injection system as in claim 12, wherein, after each predetermined volume of liquid is ejected from said cartridge, said control unit displays a visual signal.

14. A medical liquid injection system as in claim 1, wherein:
    said medical liquid injection system has a fully operational mode wherein said control unit is connected to said foot-operable pedal and wherein a plurality of injection rates and injection volumes are independently selectable through said control unit; and
    said medical liquid injection system has a limited operational mode wherein said foot-operable pedal is solely used to operate said injection system and wherein only discrete, matched pairs of injection rates and injection volumes are selectable through said foot-operable pedal.

15. A medical liquid injection system as in claim 14, wherein, in said limited operation mode, said discrete, matched pairs of injection rates and injection volumes are selectable by depressing said foot-operable pedal in discrete directions.

16. The medical liquid injection system of claim 1, wherein:
said injection system having an injection mode where said control unit emits sonorous signals after predetermined increments of said liquid are expelled from said needle.

17. A medical liquid injection system as in claim 16, wherein said control unit includes a display which displays a total current injected volume expelled from said needle.

18. A medical liquid injection system as in claim 17, wherein said control unit displays a textual or graphic final dosage message when a total injected volume reaches a predetermined desired total injected volume.

19. A medical liquid injection system as in claim 1, wherein:
said injection device includes a piston for ejecting the medical liquid from said cartridge and means for sensing a velocity of said piston; and
said foot-operable pedal includes means for monitoring said velocity of said piston and for altering a rate of rotation of said motor to achieve and maintain a desired injection rate.

20. A medical liquid injection system as in claim 19, wherein said means to monitor the velocity of said piston comprises means to detect a rate of rotation of said motor.

21. A medical liquid injection system as in claim 20, wherein said means to detect the rate of rotation of said motor comprises:
a wheel connected to said motor, said wheel including a plurality of regularly angularly-spaced apertures; and
an optical sensor for detecting passage of said apertures.

22. A medical liquid injection system as in claim 21, wherein aid optical sensor is connected to said means, in said foot-operable pedal, for monitoring said velocity and position of said piston and for altering said rate of rotation of said motor, thereby providing for monitoring and adjustment of an injection rate and a total injected volume.

23. A medical liquid injection system as in claim 1, wherein:
said hand-held liquid injection device has a body portion;
said liquid injector device includes means to rotate said cartridge case, said needle and said cartridge, independently of said body portion of said injection device, to allow desired orientation of said inclined tip of said needle without movement of said body portion of said injection device.

24. A medical liquid injection system as in claim 1, wherein said foot-operable pedal for controlling certain aspects of an injection procedure comprises:
a base;
a foot pad for engaging a foot of a user;
said foot pad being pivotally connected to said base and being pivotal about two substantially orthogonal axes;
means to detect pivoting said foot pad about each of said two substantially orthogonal axes;
means to transmit control signals to an injection device responsive to pivoting of said foot pad.

25. A medical liquid injection system as in claim 24, wherein said means to detect pivoting of said foot pad about said two substantially orthogonal axes comprises two pairs of opposed motion sensors located below said foot pad, each motion sensor being located opposite said pivotal connection between said foot pad and said base with respect an associated motion sensor, and each pair of motion sensors being aligned along one of said substantially orthogonal axes.

26. A medical liquid injection system as in claim 1, further comprising:
a harpoon for threading into a stopper of said medical liquid cartridge, said harpoon having a threaded end and a shaft having a non-circular cross section;
an assembly device for attaching said harpoon to the stopper of the medical liquid cartridge, said assembly device including:
a harpoon seat having a tubular first end and having a recess in said first end, said recess having a non-circular cross section and being sized and shaped for closely receiving said shaft of said harpoon;
a cartridge support having a through opening with first and second tubular portions, said first tubular portion being sized and shaped to closely receive said first tubular end of said harpoon seat, said second tubular portion having a diameter less than a diameter of said first tubular portion forming an abutment wall there between; and
whereby said harpoon can be reliably fixedly engaged with the stopper of the cartridge by inserting said shaft of said harpoon into said recess of said harpoon seat, inserting said first tubular end of said harpoon seat into said first tubular end of said cartridge support until said harpoon seat engages said abutment wall, inserting the cartridge into said cartridge support until the rubber stopper thereof contacts said threaded end of said harpoon, and rotating said cartridge and said cartridge support relative to said harpoon seat while applying compressive pressure.

27. A medical liquid injection system as in claim 26, wherein said harpoon includes a collar between said shaft and said threaded end to limit an amount by which said harpoon can be threaded into the rubber stopper.

28. A medical liquid injection system as in claim 1, wherein said injection device has thermal and hydraulic sealing components permitting the injector to be cleaned and sterilized in a convention manner.

* * * * *

UNITED STATES PATENT AND TRADEMARK OFFICE
CERTIFICATE OF CORRECTION

PATENT NO. : 6,520,928 B1
DATED : February 18, 2003
INVENTOR(S) : Alceu Meibach Rosa Junior It is certified that error appears in the above-identified patent and that said Letters Patent is hereby corrected as shown below:

Column 9,
Line 47, cancel "operable during a continuous" to and including "of said foot-operable pedal."

Column 10,
Line 3, change "relative d" to -- relatively low rate, for a second --

Signed and Sealed this

Twenty-second Day of July, 2003

JAMES E. ROGAN
*Director of the United States Patent and Trademark Office*